(12) United States Patent
Stensrud et al.

(10) Patent No.: US 10,519,124 B2
(45) Date of Patent: Dec. 31, 2019

(54) SYNTHESIS OF R-GLUCOSIDES, SUGAR ALCOHOLS, REDUCED SUGAR ALCOHOLS, AND FURAN DERIVATIVES OF REDUCED SUGAR ALCOHOLS

(71) Applicant: Archer Daniels Midland Company, Decatur, IL (US)

(72) Inventors: Kenneth Stensrud, Decatur, IL (US); Chi-Cheng Ma, Forsyth, IL (US); Kevin Martin, Mt. Zion, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 15/962,044

(22) Filed: Apr. 25, 2018

(65) Prior Publication Data

US 2018/0258059 A1    Sep. 13, 2018

Related U.S. Application Data

(63) Continuation of application No. 15/302,709, filed as application No. PCT/US2014/033581 on Apr. 10, 2014, now abandoned.

(51) Int. Cl.
| | | |
|---|---|---|
| *B01J 27/00* | (2006.01) |
| *C07D 307/12* | (2006.01) |
| *C07C 29/60* | (2006.01) |
| *C07C 29/132* | (2006.01) |
| *C07G 3/00* | (2006.01) |
| *B01J 23/72* | (2006.01) |
| *B01J 23/46* | (2006.01) |
| *B01J 25/00* | (2006.01) |
| *B01J 27/053* | (2006.01) |
| *B01J 27/16* | (2006.01) |
| *B01J 27/20* | (2006.01) |

(52) U.S. Cl.
CPC .......... *C07D 307/12* (2013.01); *B01J 23/462* (2013.01); *B01J 23/72* (2013.01); *B01J 25/00* (2013.01); *B01J 27/053* (2013.01); *B01J 27/16* (2013.01); *B01J 27/20* (2013.01); *C07C 29/132* (2013.01); *C07C 29/60* (2013.01); *C07G 3/00* (2013.01)

(58) Field of Classification Search
CPC ....................................................... B01J 27/00
See application file for complete search history.

(56) References Cited

U.S. PATENT DOCUMENTS 4,820,880 A * 4/1989 Urbas ..................... C07C 29/60
568/861

* cited by examiner

*Primary Examiner* — Andrew D Kosar
*Assistant Examiner* — John S Kenyon
(74) *Attorney, Agent, or Firm* — William B. Miller

(57) ABSTRACT

Disclosed herein are methods for synthesizing 1,2,5,6-hexanetetrol (HTO), 1,6 hexanediol (HDO) and other reduced polyols from C5 and C6 sugar alcohols or R glycosides. The methods include contacting the sugar alcohol or R-glycoside with a copper catalyst, most desirably a Raney copper catalyst with hydrogen for a time, temperature and pressure sufficient to form reduced polyols having 2 to 3 fewer hydoxy groups than the starting material. When the starting compound is a C6 sugar alcohol such as sorbitol or R-glycoside of a C6 sugar such as methyl glucoside, the predominant product is HTO. The same catalyst can be used to further reduce the HTO to HDO.

7 Claims, 2 Drawing Sheets

SYNTHESIS OF R-GLUCOSIDES, SUGAR ALCOHOLS, REDUCED SUGAR ALCOHOLS, AND FURAN DERIVATIVES OF REDUCED SUGAR ALCOHOLS

TECHNICAL FIELD

The present invention relates to the synthesis 1,2,5,6-hexanetetrol (HTO), 1,4,5 hexanetriol, and 1,2,6 hexanetriol from C6 sugar alcohols or R-glycosides.

BACKGROUND OF THE INVENTION

R-glycosides are known to be important intermediates for the production of fine chemicals, including sugar-based surfactants. Ordinarily, R-glycosides are prepared by Fischer glycosidation of an R-alcohol with a sugar, which involves the acid catalyzed formation of a glycoside bond between the acetal or ketal carbon of the sugar and the hydroxyl group of the alcohol. The most common sugar is glucose. R-glycosides can also be prepared by acid catalyzed Fischer glycosidation of glucose residues in a polysaccharide such as starch or cellulose with an alcohol, which results in cleavage of the glycosidic bonds in the polysaccharide via substitution of the alcohol moieties forming the free glucosides. Strong acids, elevated temperatures, and elevated pressures are typically needed. A mechanism compatible with milder conditions and utilizing a less expensive starting material, especially a starting material with otherwise limited applications, would be economically advantageous, especially on an industrial scale.

Cellulose is a primary component of plant matter, is non-nutritive, and is not widely utilized outside of the paper and textile industries. Cellulose can be converted to glucose through acid or enzymatic hydrolysis, however, hydrolysis is difficult due to the robust crystalline structure of cellulose. Known acid hydrolysis methods typically require concentrated sulfuric acid to achieve good yields of glucose. Unfortunately glucose in the presence of concentrated sulfuric acid can degrade to form hydroxymethylfurfural ("HMF") which in turn can further polymerize into a tarry substance known as humins. The formation of HMF and tarry humins negatively impacts the yield of glucose and requires additional separation steps. Enzymatic hydrolysis methods known in the art are also impractical for industrial scale conversion of cellulose to glucose due to low reaction rates and expense and enzymes do no hydrolyze cellulose that has been chemically modified.

Recently, Deng et al. reported the direct conversion of cellulose and methanol into methyl glucosides in the presence of an acid catalyst. Deng et al., *Acid-catalysed Direct Transformation of Cellulose into Methyl Glucosides in Methanol at Moderate Temperatures*, 46 Chem. Comm. 2668-70 (2010). Various dilute mineral and organic acids were tested, with sulfuric acid providing the best yield of methyl glucosides at 48%. Keggin-type heteropolyacids were also tested, with $H_3PW_{12}O_{40}$ yielding 53% methyl glucosides. However, the conversion of cellulose in ethanol in the presence of $H_3PW_{12}O_{40}$ resulted in a decreased yield of 42% ethyl glucosides. Solid acids were tested, with various forms of carbon bearing $SO_3H$ groups giving the best yield of methyl glucosides at 61%.

More recently, Dora et al. reported the catalytic conversion of cellulose into methyl glucosides over sulfonated carbon based catalysts. Dora et al., *Effective Catalytic Conversion of Cellulose into High Yields of Methyl Glucosides over Sulfonated Carbon Based Catalyst*, 120 Bioresource Technology 318-21 (2012). Carbon based catalysts containing $SO_3H$ groups were synthesized and evaluated for the conversion of cellulose in methanol. Specifically, microcrystalline cellulose was reacted with methanol and the sulfonated carbon catalyst (50% by weight of the microcrystalline cellulose) at temperatures from 175° C. to 275° C. A maximum 92% yield of methyl glucosides was obtained at a reaction time of 15 minutes at 275° C.

Turning to sugar alcohols, here are currently no known processes for producing sugar alcohols (i.e. hexitols or pentitols such as sorbitol and xylitol) from alkyl glycosides by hydrogenation. Typically sugar alcohols are produced by heating unmodified sugars at elevated pressure in the presence of a hydrogenation catalyst.

Recently, Fukuoka et al. reported that sugar alcohols could be prepared from cellulose using supported platinum or ruthenium catalysts, which showed high activity for the conversion of cellulose into sugar alcohols with the choice of support material being important. Fukuoka et al., *Catalytic Conversion of Cellulose into Sugar Alcohols*, 118 Agnew. Chem. 5285-87 (2006). The mechanism involves the hydrolysis of cellulose to glucose followed by the reduction of glucose to sorbitol and mannitol. However the yields were at best around 30% conversion to sugar alcohols, and the reactions took place at an elevated pressure of 5 MPa.

More recently, Verendel et al. reviewed one-pot conversions of polysaccharides into small organic molecules under a variety of conditions. Verendel et al., *Catalytic One-Pot Production of Small Organics from Polysaccharides*, 11 Synthesis 1649-77 (2011). Hydrolysis-by-hydrogenation of cellulose under acidic conditions and elevated pressure was disclosed as yielding up to 90% sorbitol, although these processes were categorized as "by no means simple." The direct hydrolysis-hydrogenation of starch, inulin, and polysaccharide hydrolysates to sugar alcohols by supported metals under hydrogen without the addition of soluble acids was also disclosed. Ruthenium or platinum deposited on aluminas, a variety of metals supported on activated carbon, and zeolites were reported as suitable catalysts for cellulose degradation. The effect of transition-metal nanoclusters on the degradation of cellobiose was also disclosed, with acidic conditions yielding sorbitol. A different study looked at the conversion of cellulose with varying crystallinity into polyols over supported ruthenium catalysts, with ruthenium supported on carbon nanotubes giving the best yield of 73% hexitols.

There remains a need for cost-effective methods of producing sugar alcohols with high selectivity and through alternate pathways.

On yet another subject, the molecule 1,2,5,6-hexanetetrol ("HTO") is a useful intermediate in the formation of higher value chemicals. HTO and other polyols having fewer oxygen atoms than carbon atoms may be considered a "reduced polyols." Corma et al. discloses generally that higher molecular weight polyols containing at least four carbon atoms can be used to manufacture polyesters, alkyd resins, and polyurethanes. Corma et al., *Chemical Routes for the Transformation of Biomass into Chemicals*, 107 Chem. Rev. 2443 (2007).

Sorbitol hydrogenolysis is known to produce HTO, although typically the reaction conditions are harsh and non-economical. U.S. Pat. No. 4,820,880 discloses the production of HTO involving heating a solution of a hexitol in an organic solvent with hydrogen at an elevated temperature and pressure in the presence of a copper chromite catalyst. Exemplary starting hexitols include sorbitol and mannitol.

Water was found to adversely affect the reaction speed requiring the reaction to be performed in the absence of water and instead using ethylene glycol monomethyl ether or ethylene glycol monoethyl ether as the sole solvent, which puts a solubility limit on the amount sorbitol that can be reacted. Under such conditions the maximum concentration of sorbitol that was shown to be useful was 9.4% wt/wt in ethylene glycol monomethyl ether, which provided a molar yield of about 28% HTO. In a similar reaction where the sorbitol concentration was reduced to about 2% wt/wt in glycol monomethyl ether, the molar yield of HTO was 38% however the low concentration of reactants makes such a process uneconomical. More recently, U.S. Pat. No. 6,841,085 discloses methods for the hydrogenolysis of 6-carbon sugar alcohols, including sorbitol, involving reacting the starting material with hydrogen at a temperature of at least 120° C. in the presence of a rhenium-containing multimetallic solid catalyst. Nickel and ruthenium catalysts were disclosed as traditional catalysts for sorbitol hydrogenolysis, however these catalyst predominantly produced lower level polyols such as glycerol and propylene glycol and were not shown to detectably produce HTO or hexanetriols.

There remains a need for improved cost-effective catalyst for producing HTO from sugar alcohols and a need for alternative substrates other than sugar alcohols.

On another background subject, the molecule 2,5 bis (hydroxymethyl)tetrahydrofuran ("2,5-HMTHF") is typically prepared by the catalyzed reduction of HMF. This is impractical due to the expense of HMF, harsh reaction conditions, and poor yields. For example, U.S. Pat. No. 4,820,880 discloses the conversion of HTO to 2,5-HMTHF in ethylene glycol monomethyl ether with hydrogen at a pressure of at least 50 atmospheres, in the presence of a copper chromite catalyst, at a temperature in the range of 180° C. to 230° C.

Overall, there is a need in the art to devise economical methods for converting cellulose to alkyl glycosides, for converting alkyl glycosides to sugar alcohols, for converting sugar alcohols to HTO and other reduced polyols, and for making useful derivatives of such reduced polyols such as 2,5-HMTHF.

SUMMARY OF THE INVENTION

The present disclosure provides, in one aspect, methods of synthesizing R-glycosides from acetyl cellulose pulp substantially without the formation of degradation products. These methods involve heating an acetyl cellulose pulp in the presence of an alcohol of the formula ROH, where R is a $C_1$-$C_4$ alkyl group, and an acid catalyst selected from the group consisting of phosphonic acid and a sulfonic acid, for a time and at a temperature sufficient to form an R-glycoside fraction from the acetyl cellulose pulp. In preferred practices the acetyl cellulose pulp is derived from a monocot species, for example, a species selected from the group consisting of grasses, corn stover, bamboo, wheat straw, barley straw, millet straw, sorghum straw, and rice straw. In exemplary embodiments the acid catalyst is a sulfonic acid of the formula $R^1SO_3H$ where R is an alkyl or cycloalkyl group.

In another aspect the present disclosure provides methods of synthesizing sugar alcohols from alkyl glycosides. These methods include contacting a solution containing an R-glycoside with a hydrogenation catalyst for a time and at a temperature and a pressure sufficient to convert the R-glycoside to a mixture comprising the sugar alcohol and ROH, where R is a $C_1$-$C_4$ alkyl group. The hydrogenation catalyst may contain copper and/r ruthenium. When the hydrogenation catalyst comprises copper and the solution should contains less than 2 ppm sulfide anion and less than 1 ppm chloride anions. Exemplary ruthenium catalysts are selected from the group consisting of ruthenium supported on carbon, ruthenium supported on a zeolite, ruthenium supported on $TiO_2$, and ruthenium supported on $Al_2O_3$.

In another aspect the foregoing method are combined providing a method of producing sugar alcohols from acetylated cellulose pulp that includes generating an R-glycoside from acetyl cellulose pulp as described above; and contacting the R-glycoside with a hydrogenation catalyst as further described above.

In another aspect the present disclosure provides methods of making a reduced sugar alcohol including at least one member selected from the group consisting of 1,4,5 hexanetriol, 2,6-hexanetetrol, and 1,2,5,6 hexanetetro. These methods include contacting a solution comprising water and at least 20% wt/wt of a starting compound selected from the group consisting of a C6 sugar alcohol and a R-glycoside of a C6 sugar, wherein R is a methyl or ethyl group, with hydrogen and a Raney copper catalyst for a time and at a temperature and pressure sufficient to produce a mixture containing one or more of the a reduced sugar alcohols with a combined selectively yield of at least 50% mol/mol. In most advantageous embodiments of these methods the reaction solution comprises 20-30% wt/wt water and 45-55% of a C2-C3 glycol. In an exemplary embodiment the solution comprises 20-30% wt/wt water and 50-55% wt/wt propylene glycol. These methods provide of a combined selectivity yield for ther reduced sugar alcohols of at least 70% mol/mol. One specific embodiment of these methods is a method of making 1,2,5,6-hexanetetrol. This specific embodiment includes contacting a solution comprising 20-30% wt/wt water, 45-55% of propylene glycol and at least 20% wt/wt of a starting compound selected from the group consisting of C6 sugar alcohol and a R-glycoside of a C6 sugar, wherein R is a methyl or ethyl group, with hydrogen and a Raney copper catalyst for a time and at a temperature and pressure sufficient to produce a mixture containing the 1,2,5,6-hexanetetrol with a selectively yield of at least 35% wt/wt. In most advantageous embodiments the selectivity yield for 1,2,5,6-hexanetetrol is at least 40% wt/wt.

In yet another aspect, there is provided methods of making tetrahydrofuran derivatives such as 2,5-bis(hydroxymethyl)tetrahydrofuran from the reduced sugar alcohol. In one embodiment these methods include contacting a mixture comprising 1,2,5,6-hexanetetrol with an acid catalyst selected from the group consisting of sulfuric acid, phosphonic acid carbonic acid and a water tolerant non-Bronsted Lewis acid for a time and at a temperature and a pressure sufficient to convert the 1,2,5,6-hexanetetrol to 2,5 bis(hydroxymethyl)tetrahydrofuran. In exemplary embodiments the non-Bronsted Lewis acid is a triflate compound such as of bismuth triflate and scandium triflate. In other exemplary embodiments the acid acatalyst is sulfuric acid. In a preferred embodiment the acid catalyst is phsosphonic acid.

In certain embodiments, the mixture further includes 1,4,5 hexanetriol and contacting with the acid catalyst further converts the 1,4,5 hexanetriol to 2-hydroxyethyl tetrahydrofuran. In certain embodiments the method includes making 2 hydroxyethyl tetrahydrofuran by contacting a mixture comprising 1,4,5 hexanetriol with the same type of acid catalysts. Further methods may further include separating the 2-hydroxyethyl tetrahydrofuran from the 2,5-bis(hydroxymethyl)tetrahydrofuran. In a particular further embodiment the separated 2,5 bis(hydroxymethyl) tetrahydrofuran is contacted with a rhenium oxide catalyst for a time and a temperature sufficient to convert the 2,5-bis (hydroxymethyl)tetrahydrofuran to 1,6 hexanediol.

DETAILED DESCRIPTION OF THE INVENTION

Figure 1:
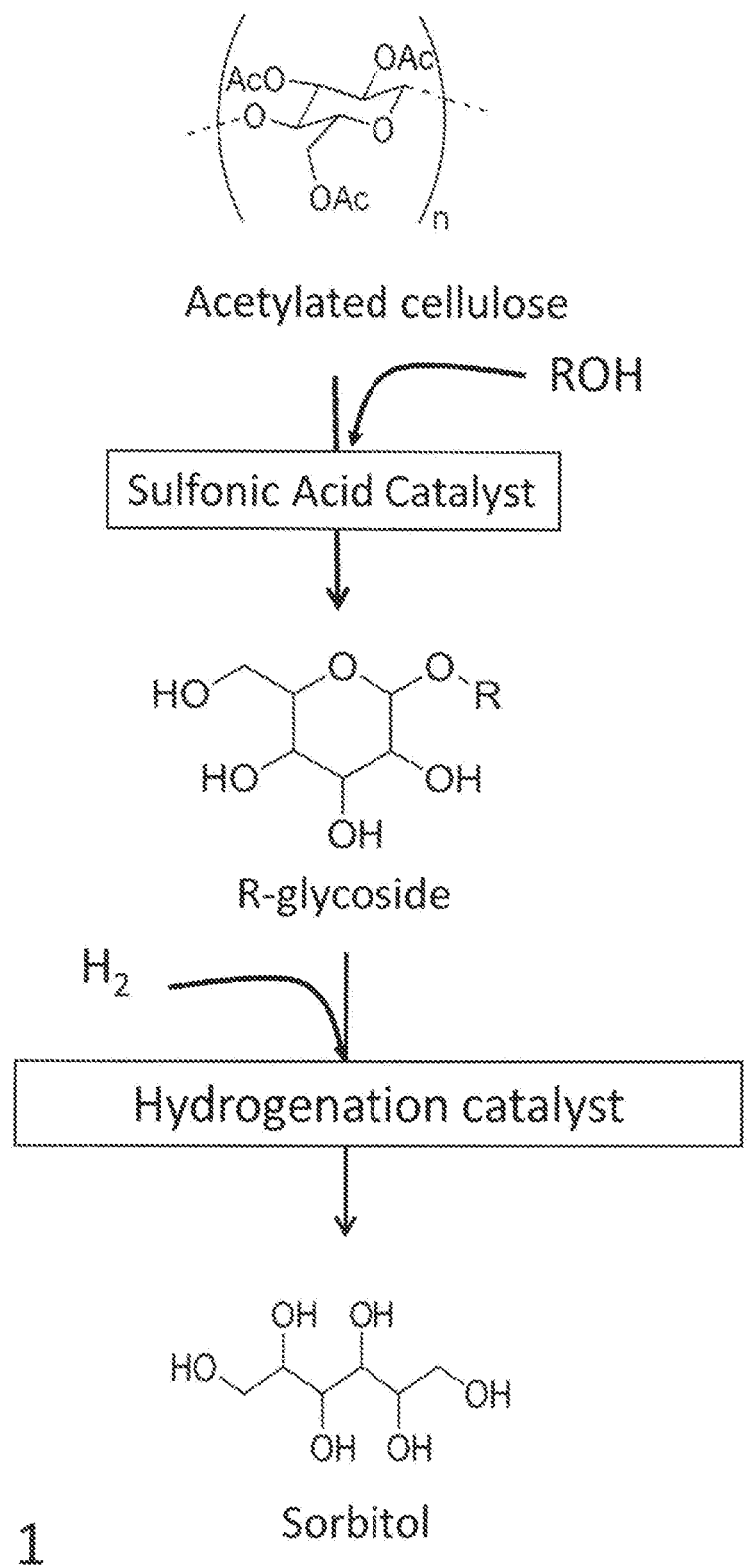
FIG. 1 shows synthesis of R glucosides from acetylated cellulose over an acid catalyst in the presence of an R alcohol, and synthesis of sorbitol from R-glucosides via hydrogenolysis over a hydrogenation catalyst according to certain aspects of the invention.

Synthesis of R-Glycosides from Acetyl Cellulose Pulp.

The present disclosure provides, in one aspect, methods of synthesizing R-glycosides from acetyl cellulose pulp in the presence of an alcohol and an acid catalyst. "R" as used generically in chemical formulae throughout the present disclosure represents an alkyl moiety. Glycosides generically refer to a substance containing a glycosidic bond (i.e. a type of covalent bond that joins a sugar molecule to another functional group, in this case an alkyl moiety), while glucosides generically refer to glycosides derived from glucose.

The acetyl cellulose pulp most suitable for use in the methods of the present disclosure is derived from a monocot species. Preferably, the monocot species is selected from the group consisting of grasses, corn stover, bamboo, wheat straw, barley straw, millet straw, sorghum straw, and rice straw. More preferably the monocot species is corn stover. The acetyl cellulose pulp may be prepared by any method known in the industry. One non-limiting example of the preparation of an acetylated cellulose pulp, disclosed in WIPO Publication No. WO 2013/044042, involves treatment of lignocellulosic biomass with a $C_1$-$C_2$ acid (i.e. an acid containing 1 or 2 carbon atoms) followed by washing with a $C_1$-$C_2$ acid-miscible organic solvent.

The alcohols most suitable for use in the methods of the present disclosure are those containing between 1 and 4 carbon atoms: methanol, ethanol, propanol, butanol, and isomers thereof. The alcohol is preferably present in at least a 5:1 weight ratio of alcohol to acetyl cellulose pulp The acid catalyst most suitable for use in the methods of the present disclosure sulfonic acids of the formula RSO3H or phsosphonic acid. Suitable, but non-exclusive examples of sulfonic acids include dinonylnaphthalene sulfonic acid, 6-amino-m-toluenesulfonic acid (also known as 2-amino-5-methylbenzene sulfonic acid), alkylbenzene sulfonic acids (sold as Calsoft® LAS-99, which is a linear alkylbenzene sulfonic acid comprising a minimum 97% of C10-C16 alkyl derivatives of benzenesulfonic acid), branched dodecylbenzene sulfonic acid (sold as Calimulse® EM-99), and alkylarylsulfonic acid (sold as Aristonic® acid). The acid catalyst may be homogeneous or heterogeneous. The acid catalyst is preferably present in an amount of at least 0.5% by weight of the alcohol and for economic reasons, preferably not more than 4% by weight of the alcohol.

In a typical process the acetyl cellulose pulp is first washed in the alcohol of choice, which is most typically methanol or ethanol, although any $C_1$-$C_4$ alcohol may be used. The washed acetyl cellulose pulp is combined with the alcohol and an acid catalyst in a reaction vessel and heated for a time and at a temperature sufficient to form an R-glycoside fraction from the acetyl cellulose pulp. The reaction vessel is then cooled to room temperature. Typically the contents are filtered to remove residual unreacted pulp. The liquid fraction may be further subjected to standard separation methods such as liquid extraction or distillation to yield a purified R-glycoside fraction.

In the methods for synthesizing R-glycosides provided herein, reaction time and temperature can be varied. At temperatures above 250° C. degradation products negatively impact the yield of R-glycosides. At temperatures below 150° C., the acetyl cellulose pulp is not substantially solubilized and the yield of R-glycosides is also negatively impacted. The preferred reaction temperature is therefore 150-250° C. The range of reaction times in the methods provided herein is typically between 15 minutes and 45 minutes. Heating the acetyl cellulose pulp at these temperatures and times solubilizes the acetyl cellulose pulp, solubilizes hydrophobic sulfonic acid catalysts, and allows for the formation of an R-glycoside fraction while avoiding the formation of significant amounts of degradation products such as HMF.

Typically, the yield of R-glycosides from these methods is between 20% and 60% of the weight of the starting sugars in the acetyl cellulose pulp. Other side products of the methods may include levoglucosan, levulinates, furfurals such as hydroxymethyl furfural (HMF), and some soluble free sugars such as dextrose.

Synthesis of Sugar Alcohols from R-Glycosides.

The present disclosure provides, in another aspect, methods of synthesizing sugar alcohols from R-glycosides in the presence of hydrogen and a hydrogenation catalyst as depicted in FIG. 1. An Sugar alcohols that can be synthesized by the present methods include, but are not limited to, sorbitol, mannitol, iditol, dulcitol, talitol, and 1,4-sorbitan.

The R-glycoside can be obtained from a commercial source or derived from any known method in the industry. In certain embodiments the R-glycoside is derived from acetyl cellulose pulp according to the previously described methods, and therefore the alkyl moiety of the R-glycoside preferably contains between 1 and 4 carbon atoms. Other catalysts such as various copper catalysts may also be useful. When the hydrogenation catalyst is selected as one containing copper, the R-glycoside should contain minimal anions, specifically less than 2 ppm sulfide anions and less than 1 ppm chloride anions.

The hydrogenation catalyst is preferably acidic. Hydrogenation catalysts containing ruthenium, including but not limited to ruthenium supported on carbon, ruthenium supported on a zeolite, ruthenium supported on $TiO_2$, and ruthenium supported on $Al_2O_3$, particularly favor the synthesis of sugar alcohols. The hydrogenation catalyst is preferably present in an amount of 0.5-12.5% weight of the R-glycoside. In exemplary practices using ruthenium on carbon the amount was about 5% by weight of the R-glycoside.

The methods include combining the R-glycoside, hydrogenation catalyst, and water in a reactor vessel. Air is removed from the reactor vessel and hydrogen is charged to a desired pressure at room temperature. The reactor is then heated to a temperature for a time sufficient to convert the R-glycoside to a mixture comprising a sugar alcohol. The temperature should be at least 150° C. and the pressure at least 600 psi. Lower temperatures and pressures result in substantially reduced yield of the sugar alcohol. Suitable temperatures are between 160° C. and 220° C. Most typically the temperature should between 170° C. and 190° C., with a temperature of about 180° C. being most preferred. Suitable pressures are 600-1000 psi, with exemplary pressures being about 850 psi. The reaction time is typically 2-4 hours.

Under preferred conditions the R-glycoside conversion rate reaches nearly 100% with a molar conversion rate to sorbitol of at least 85% In certain non-limiting examples using purified R-glycosides the molar conversion rate reached 97% or even 100%, Synthesis of 1,2,5,6-Hexanetetrol and Hexanetriols.

In another aspect, the present disclosure provides methods of synthesizing a desired compound including at least one member selected from the group consisting of 1,4,5 hexanetriol, 1,2,5,6 hexanetetrol, and 1,2,6-hexanetriol, from a starting compound that is a C6 R-glycoside or C6 sugar alcohol present as at least 20% wt/wt in s solution comprising water by hydrogenation with hydrogen in the presence of a Raney copper catalyst. The Raney copper catalyst may be obtained from a commercial source (e.g., WR Grace & Co, United States) or prepared by methods known to those of ordinary skill in the art. Typically the method of preparation of a Raney copper catalyst involves alkali treatment of a copper aluminum alloy to etch away aluminum from a surface portion of the alloy.

Preferably, the Raney copper catalyst is deployed as a fixed bed in a reactor and is present at 5%-30% of the weight of the starting compound. In contrast to the copper chromite catalyst described in U.S. Pat. No. 4,820,080 or other copper catalysts such as sponge copper (see Example 6) the reaction with Raney copper can be performed in the presence of water with high molar selectivity for, 1,2,5,6 hexanetetrol, 1,4,5 hexanetriol and 1,2,6-hexanetriol, which permits the starting material to be dissolved to 50% wt/wt or more of the reaction mixture when water is the only solvent, with the combined selectivity for the desired compounds is at least 50% mol/mol.

Although in some embodiments water may be the only solvent, in particularly advantageous embodiments the solvent is a mixture of 20-30% wt/wt water and 45-55% wt/wt of a C2-C3 glycol. In this case the starting material can be from 15% to 35% wt/wt of the reaction mixture. In the most advantageous embodiments the C2-C3 glycol is propylene glycol. In preferred practices the starting material (C6 sugar alcohol or C6 alkyl glycoside) is at least 20% wt/wt of the reaction mixture. In exemplary embodiments the starting material is about 25% wt/wt of the reaction mixture. While not being bound by theory, it is believed the mixture of water and propylene glycol strikes an optimal balance of having enough water to solubilize up to 35% of the starting material while the presence of enough C2-C3 glycol permits more hydrogen to be solubilized in the reaction mixture and further prolonging the lifespan of the Raney copper catalyst. When the starting material is a C6 R-glycoside or C6 sugar alcohol, the reaction with Raney copper under these conditions has a high selectivity for HTO and 1,4,5 hexanetriol, with these combined species accounting for over 60% and in most case over 70% of the molar yield. Typically the HTO itself accounts for at least 35% and more typically at least 40% of the molar yield from the starting material.

A first subset of the methods involves the synthesis of HTO from C6 R-glycosides in the presence of the Raney copper catalyst. The R-glycoside can be obtained from a commercial source or derived from any known method in the industry. In certain embodiments the R-glycoside is an ethyl glucoside obtained from actylated cellulose pulp as previously described herein. The reaction, however, can use any R-glycoside where the R group is a C1 to C4 alkyl group. Most preferably the R group is methyl or ethyl, with the most commonly available glycosides being methyl glucoside or ethyl glucoside.

A second subset of the methods involves the synthesis of HTO from C6 sugar alcohols in the presence of the same catalyst. The sugar alcohols can be obtained from a commercial source or derived from any known method in the industry. In certain embodiments the sugar alcohols may be obtained by hydrogenation of C6 sugars or C6 R-glycosides. For example, sorbitol is typically obtained by hydrogenation of glucose over a Raney nickel catalyst. Ethyl glucoside may be obtained hydrogenation of an acetyl cellulose pulp according to the methods previously described herein.

The methods include in one aspect, combining the R-glycoside or sugar alcohol with water and optionally and more preferably with the C2-C6 glycol in a reaction vessel preferably containing a fixed bed of Raney copper. Air is removed from the reactor vessel and hydrogen is charged to a specified pressure at room temperature. The reactor is then heated to a temperature and for a time sufficient to convert the starting materials to-a mixture containing the desired materials, which in the case of C6 sugar alcohol or C6 R-glycoside will be a mixture of HTO and 1,4,5 hexanetriol. Under the best reaction conditions over 98% of the starting material is converted with a selectivity for HTO and 1,4,5 hexanetriol being least 50% mol/mol when only water is used or greater than 60% and even greater than 70% when a combination of water and C2 or c3 glycol such as propylene glycol is used as the solvent. Under such conditions HTO is least 35% and more preferably at least 40% of the mo/mol yield from the starting material.

In the methods for synthesizing HTO provided herein, the pressure, temperature, and reaction time can be varied. Preferably the temperature is between 175° C. and 250° C. In exemplary embodiments the temperature 190° C.-215° C. The pressure is preferably between 500 psi and 2500 psi. In more typical embodiments the pressure is between 800 and 2000 psi. In certain exemplary embodiments the pressure is about 1800 psi. In a batch reactor, the reaction time is preferably between 1 hour and 4 hours, and more preferably is 3 hours. In a continuous reaction system the input stream of starting materials and the flow rate of hydrogen are adjusted to obtain an optimal residence time of the starting materials in contact with the Raney copper catalyst. In typical laboratory scale examples, the hydrogen flow rate was 800-1000 milliliters/minute and the sorbitol solution flow rate was 0.25 milliliters/minute obtaining an average residence time of 2 hours.

In addition to the major hexanetriols discussed above, the same methods of hydrogenolysis of C6 sugars or R-glucosides produce other polyols, such as 1,2,5 hexanetriol, 1,2 butanediol, 1,2,3 butanetriol, propylene glycol, ethylene glycol and small amounts. Under conditions where HTO synthesis is optimum, such as in the presence of propylene glycol and water, 1,2 butanediol is the third major product made after HTO and 1,4,5 hexanetriol.

Similarly, C5 sugar alcohols such as ribotol, xylitol and arabitol, and R-glycosides may also be subject to hydrogenolysis over Raney nickel as provided herein, resulting in the production of 1,2,5 pentanetriol as the dominant product, along with 1,2 butanediol, 1,2,4 butanetriol, glycerol, ethylene glycol and propylene glycol. Erythritol may also be reduced by hydrogenolysis over Raney nickel to form 1,2 buatnediol as the dominant product, along with 1,2,4 butatnetriol, 2,3 butatanediol, propylene glycol and ethylene glycol.

Intramolecular Cyclization of Polyols to Tetrahydrofuran Derivatives

Figure 2:
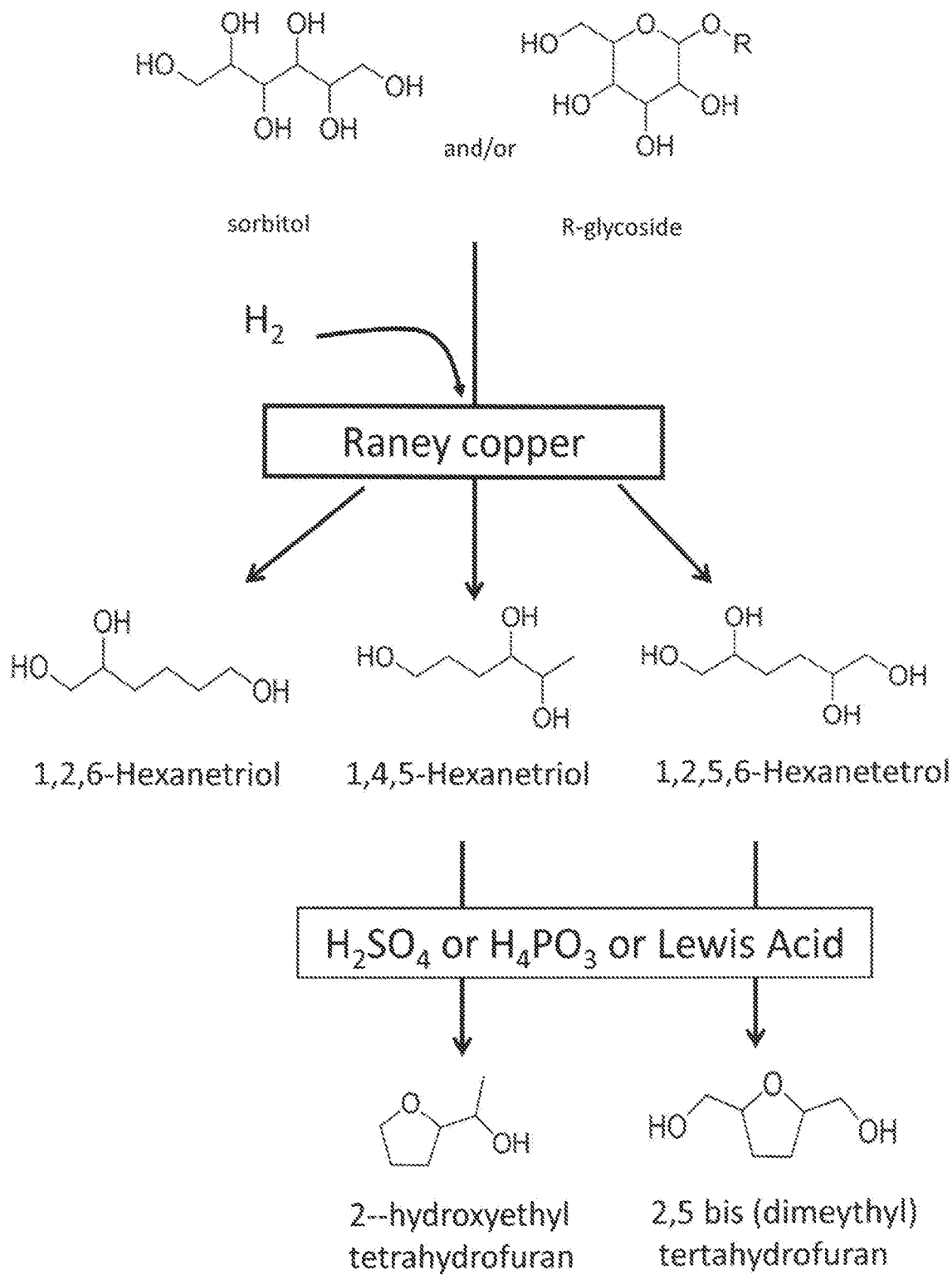
FIG. 2 shows synthesis of hexanetriols and 1,2,5,6 hexanetetrol via hydrogenolysis of sorbitol and/or a C6 R-glucoside over a Raney nickel catalyst according to other aspects of the invention, and shows synthesis of 2,5 (hydoxymethyl) tetrahydrofuran from 1,2,5,6 hexanetetrol, and synthesis 2-hydroxyethyl tetrahydrofuran from 1,4,5 hexanetriol, each by contact with a non-Bronsted Lewis acid according to yet another aspect of the invention.

An important use of HTO and the hexanetriols, particularly 1,4,5 hexanetriol, is that these molecules can readily undergo intermolecular cyclization in the presence of an acid to form useful tetrahydrofuran (THF) derivatives as shown in FIG. 2. The cyclization reaction is a dehydration, which releases a water molecule form the polyols. The two dominant polyols from Raney nickel catalyzed hydrogenolysis of a C6 sugar alcohol are HTO and 1,4,5 hexanetriol. HTO undergoes cyclization to form 2,5-bis(hydroxymethyl)tetrahydrofuran (2,5 HMTHF) which is useful starting material for the preparation of polymers or 1,6 hexanediol. Under the same conditions 1,4,5 hexanetriol undergoes cyclization to form 2-hydoxyethyl tetrahydyrofuran, which is a valuable solvent and useful in the pharmaceutical field. Advantageously, the acid catalyzed intramolecular cyclization of these compounds to their respective THF derivatives allows for easy separation of the THF derivatives from one another and from the starting sugar alcohols and hexane polyols that may remain unreacted.

As mentioned in preferred embodiments the acid catalyst is preferably selected from the group consisting of sulfuric acid, phsosphonic acid, carbonic acid or a water tolerant non-Bronsted Lewis acid. It was surprisingly discovered that phosphonic acid present as a homogenous catalyst works exceptionally well, while phosphoric acid does not work at all under most conditions. It may also be the case that heterogenous phosphonic acid catalysts uch as were used for formation of glycosides, may also be useful.

A water tolerant non-Bronsted Lewis acid is a molecular species that accepts electrons in the manner that hydrogen accept electrons in a Bronsted acid, but uses an acceptor species other than hydrogen, and that is resistant to hydrolysis in the presence of water. Exemplary water tolerant non-Bronsted Lewis acids are triflate compound exemplified herein by bismuth (III) triflate and scandium (III) triflate. Other suitable triflates include, but are not limited to, silver (I) triflate, zinc (II) triflate, gallium (III) triflate, neodymium (III) triflate, aluminum triflate, indium (III) triflate, tin (II) triflate, lanthanum (III) triflate, iron (II) triflate, yttrium (III) triflate, thallium (I) triflate, gadolinium (III) triflate, holmium (III) triflate, praseodymium (III) triflate, copper (II) triflate, samarium (III) triflate, ytterbium (III) triflate hydrate, and nickel (II) triflate. Other suitable water tolerant non-Bronsted Lewis acids include, but are not limited to, bismuth (III) chloride, indium chloride tetrahydrate, tin (II) chloride, aluminum chloride hexahydrate, silver (I) acetate, cadmium sulfate, lanthanum oxide, copper (I) chloride, copper (II) chloride, lithium bromide, and ruthenium (III) chloride. Preferably the acid catalyst is present in the range of 0.05% to 5% mol/mol of the starting materials in the reaction mixture. Still another alternative acid catalyst is carbonic acid, which can be generated performing the reaction in water, under pressure and in the presence of carbon dioxide.

The methods comprise combining HTO, any of the hexanetriols or a mixture of the same with or without any residual unreacted sugar alcohol or 6C R-glycoside with the acid catalyst. In one practice the HTO and the hexanetriols may first be separated form one another, for example by distillation. In other practices the entire reaction mixture resulting from hydrogenolysis of the sugar alcohol or 6C R-glycoside over Raney copper can be used and the subsequent THF derivative separated thereafter by distillation, In the case where the acid catalyst is sulfuric acid or a non-Bronsted Lewis acid compound, the reaction mixture is preferably placed under vacuum of less than 0.4 psi and heated for a time sufficient to convert the hexanetriols and the HTO to their respective tetrahydrofuran derivatives described above. When the reaction is done in the presence of carbonic acid, it performed under pressure, typically at least 625 psi.

In the methods provided herein, the temperature, pressure, and reaction time can be varied. When the acid catalyst is not generated from $CO_2$, the temperature is preferably between 110° C. and 150° C. In methods using sulfuric acid or triflate catalysts, the temperature, pressure, and reaction time can be varied. Preferably the temperature is between 120° C. and 150° C. Temperatures below 120° C. fail to provide sufficient thermal energy to effectuate ring closure. Temperatures above 150° C. induce formation of unwanted side products. When a triflate, such as bismuth triflate or scandium triflate is used as the acid catalyst, the temperature is more preferably about 130° C.

Further, the acid catalyzed cyclization preferably takes place under vacuum to facilitate removal of the water formed by the dehydration and subsequent recovery the desired THF derivative products. The vacuum is preferably within the pressure range of 3.0 to 6.0 psi. Pressures below 3.0 psi may cause some of the desired THF derivatives having low boiling points and high vapor pressures to evaporate. Pressures above 6.0 psi fail to remove the water formed during the reaction. Lower pressures such as less than 0.4 psi, or even 0.1 psi are useful for the subsequent recovery of THF derivatives with lower vapor pressures and/or higher boiling points.

Suitable reaction times are 1 to 4 hours. In some embodiments the reactions are complete in less 1-2 hours, and in some embodiments about 1 hour.

The non-Bronsted Lewis acid catalysts useful herein are all water tolerant. Preferably the non-Bronsted Lewis acid catalyst is a metal triflate. Preferably the non-Bronsted Lewis acid catalyst is homogeneous. In particular embodiments, the non-Bronsted Lewis acid catalyst is selected from the group consisting of bismuth triflate and scandium triflate. The triflate acid catalyst load is preferably between 0.5 mole percent and 5 mole percent based on the starting polyol, and more preferably present in an amount of 1 mole percent based on the starting polyol materials.

In addition to the above compounds, other polyols obtained by Raney nickel catalyzed hydrogenation of C6 sugar alcohols or R-glucosides include, 1,2,6 hexanetriol, 1,2,5 hexane triol and 1,2,4 butanetriol. Acid catalyzed cyclization of these compound predominantly forms 1-methanol tetrahydropyranol, 5-methyltetrahydrofuran 2-methanol, and 3-hydroxy tetrahydrofuran, respectively.

Further, a C5 sugar alcohols may also be reduced to lower polyols over Raney nickel. When a C5 sugar alcohol is used, the dominant reduced polyol is 1,2,5 pentanetriol. Acid catalyzed cyclization of this compound predominantly forms tetrahydrofuran-2 methanol.

As shown in Table 1 below, clearly full conversion of the polyols to their cyclized derivatives is possible. As demonstrated in Table 1 and by certain non-limiting examples, when nearly full conversion of the starting sugar alcohol was achieved, up to a 83% mol/mol yield the cyclized THF derivatives can be obtained from their respective starting polyol compounds. As used herein, "nearly full conversion" means at least 97% of the starting compound or compounds are consumed in the reaction.

TABLE 1

% conversion to cyclic derivatives

| | total % conversion | total % cyclized products | % cyclized products from converted products |
|---|---|---|---|
| 1,2,5,6 hexanetetrol, crude mixture | 25% | 17% | 68.00% |
| 1,2,5,6 hexanetetrol, crude mixture | 28% | 21% | 75.00% |
| 1,2,5,6 hexanetetrol, pure | 99% | 62% | 62.63% |
| 1,2,5 pentanetriol, pure | 64% | 50% | 78.13% |
| 1,2,4 butanetriol, pure | 88% | 76% | 86.36% |
| 1,2,5 hexanetriol pure | 100% | 83% | 83.00% |

The 2,5-bis(hydroxymethyl) tetrahydrofuran and other THF (and pyran) derivatives made from the polyols can be readily separated from one another and from unreacted polyols by distillation. The 2,5-bis(hydroxymethyl) tetrahydrofuran can be subsequently converted to 1,6 hexanediol via oxidation of the furan ring by contact with a rhenium oxide catalyst for a time and a temperature sufficient to convert the 2,5-bis(hydroxymethyl)tetrahydrofuran to 1,6 hexanediol. Preferably the rhenium oxide catalyst further includes silicon oxide.

The examples that follow are provided to illustrate various aspects of the invention and are not intended to limit the invention in any way. One of ordinary skill in the art may use these examples as a guide to practice various aspects of the invention with different sources of acetyl cellulose pulp, different alcohols, different acid catalysts, different hydrogenation catalysts, different polyol mixtures, or different conditions without departing from the scope of the invention disclosed.

Example 1: Preparation of Ethyl Glycosides from Aceytlated Corn Stover Pulp

Acetylated corn stover pulp obtained by the method described in PCT Publication No. WO 2013/044042 was washed with ethanol, filtered, oven dried, and ground. A 75 milliliter autoclave reactor was charged with 2 grams of the washed, ground pulp, 40 grams of denatured ethanol, and 0.2 grams of methanesulfonic acid. The reactor system was heated to 185° C. After the set temperature was reached the reactor contents were held at 185° C. for 30 minutes. The reactor was cooled to room temperature and the contents were filtered. About 0.84 grams of dried, residual pulp was removed from 44.14 grams of filtrate. The yield of ethyl glucosides in the filtrate as a weight percent of the sugars from the starting solubilized pulp was 34%.

Example 2: Preparation of Methyl Glycosides from Aceytlated Corn Stover Pulp Acetylated corn stover pulp was washed with ethanol, filtered, oven dried, and ground. A 75 milliliter autoclave reactor was charged with 2 grams of the washed, ground pulp, 40 grams of methanol, and 0.2 grams of methanesulfonic acid. The reactor system was heated to 185° C. After the set temperature was reached, the reactor contents were held at 185° C. for 30 minutes. The reactor was cooled to room temperature and the contents were filtered. About 0.93 grams of dried, residual pulp was removed from 44.72 grams of filtrate. The yield of monomethyl glucosides in the filtrate as a molar percent of the starting sugars in the pulp was 45%.

Example 3: Preparation of Methyl Glycosides from Aceytlated Corn Stover Pulp—Various Acids The procedure described in Example 2 was followed using various reaction times and temperatures and various acids resulting in the molar yields of monomethyl glucosides shown in Table 2. EM-99 is a branched dodecylbenzene sulfonic acid (sold as Calimulse® EM-99), LAS-99 is alkylbenzene sulfonic acids (sold as Calsoft® LAS-99), pTSA is para-toluene sulfonic acid, MSA is methanesulfonic acid.

TABLE 2

| Acid | EM-99 | LAS-99 | pTSA | MSA |
|---|---|---|---|---|
| Temp C. | 185 | 185 | 200 | 185 |
| Time (min) | 15 | 15 | 30 | 30 |
| molar yield of products from initial dextrose | | | | |
| HMF | 0.19 | 0.22 | 0.56 | 0.31 |
| methyl levulinate | 1.34 | 5.49 | 8.21 | 22.1 |
| dextrose | 3.47 | 2.98 | 4.3 | 2.39 |
| levoglucosan | 1.56 | 1.4 | 2.58 | 1.48 |
| total monomethyl glucosides | 48.31 | 45.17 | 55.55 | 45.02 |

Example 4: Preparation of Sorbitol from Methyl Glucoside—Lower Temperature

A mixture of 80.1 grams of methyl glucoside, 10.1 grams of Ru/C, and 300 milliliters of water was added to an autoclave reactor fitted with temperature and pressure controllers. Air was removed by bubbling hydrogen through the dip-tube 3 times. Hydrogen was charged at 850 psi at room temperature. The mixture was heated to 140° C. and held at that temperature for 3 hours. The reactor was cooled to room temperature and the remaining hydrogen was released. The reactor contents were filtered to remove the catalyst. The filtrate was evaporated under vacuum to obtain less than 5% yield of sorbitol and a large amount of unreacted methyl glucoside.)

Example 5: Preparation of Sorbitol from Methyl Glucoside—Higher Temperature

A mixture of 80.1 grams of methyl glucoside, 10.1 grams of Ru/C, and 300 milliliters of water was added to an autoclave reactor fitted with temperature and pressure controllers. Air was removed by bubbling hydrogen through the dip-tube 3 times. Hydrogen was charged at 850 psi at room temperature. The mixture was heated to 165° C. and held at that temperature for 3 hours. The reactor was cooled to room temperature and the remaining hydrogen was released. The reactor contents were filtered to remove the catalyst. The filtrate was evaporated under vacuum to obtain 97% yield of sorbitol and a small amount of unreacted methyl glucoside.

Example 6: Preparation of Sorbitol from Methyl Glucoside

A mixture of 80.1 grams of methyl glucoside, 10.1 grams of Ru/C, and 300 milliliters of water was added to an autoclave reactor fitted with temperature and pressure controllers. Air was removed by bubbling hydrogen through the dip-tube 3 times. Hydrogen was charged at 850 psi at room temperature. The mixture was heated to 180° C. and held at that temperature for 3 hours. The reactor was cooled to room temperature and the remaining hydrogen was released. The reactor contents were filtered to remove the catalyst. The filtrate was evaporated under vacuum to obtain 100% yield of sorbitol.

Example 7: Preparation of 1,2,5,6 Hexanetetrol from Methyl Glucoside in Water with Sponge Copper Catalyst—Comparative Example A mixture of 80.1 grams of methyl glucoside, 24.8 grams of sponge copper, and 300 milliliters of water was added to an autoclave reactor fitted with temperature and pressure controllers. Air was removed by bubbling hydrogen through a dip-tube 3 times. Hydrogen was charged at 850 psi at room temperature. The mixture was heated to 225° C. and held at that temperature for 3 hours. The reactor was cooled to room temperature and the remaining hydrogen was released. The reactor contents were filtered to remove the catalyst. The filtrate was evaporated under vacuum to obtain 1,2,5,6-hexanetetrol (15% wt/wt) and sorbitol (85% wt/wt).

Example 8: Preparation of 1,2,5,6 Hexanetetrol from Sorbitol in Water with Raney Copper Low Pressure A Raney copper catalyst was loaded into a fixed bed reactor system. The reactor was charged with hydrogen at 600 psi, and the hydrogen flow rate was maintained at 1000 milliliters/minute. The reactor was heated to 225° C. A solution of 50% wt/wt sorbitol and water was fed through the reactor system at a rate where LHSV=0.5 The conversion of sorbitol was 98.5%, with a 5.8% weight yield of 1,2,5,6-hexanetetrol.

Example 9: Preparation of 1,2,5,6 Hexanetetrol from Sorbitol in Water with Raney Copper—High Pressure Raney copper catalyst was loaded into a fixed bed reactor system as in example 7. Hydrogen was charged at 1800 psi, and the hydrogen flow rate was maintained at 1000 milliliters/minute. The reactor was heated to 205° C. Again a solution of 50% wt/wt sorbitol and water was fed through the reactor system at a rate where LHSV=0.5. The conversion of sorbitol was 73%, with a 28.8% selective weight yield of 1,2,5,6-hexanetetrol. Other polyols were present but not quantified.

Example 10 Preparation of 1,2,5,6-Hexanetetrol from Sorbitol in Water/Propylene Glycol with Raney Copper Solutions containing 25% wt/wt sorbitol, about 25% wt/wt water and about 50% weight propylene glycol as shown in Table 3 were passed through a Raney copper fixed bed reactor system as described in Examples 8 and 9, at 210° C. and a pressure of 1800 psi. The resulting reaction mixture was analyzed for propylene glycol (PG), ethylene glycol (EG) 1,2 hexanediol (1,2-HDO), 1,2 butanediol (1,2-BDO), 1,2,6 hexanetriol, (1,3,6-HTO), 1,4,5 hexanetriol (1,4,5-HTO) and 1,2,5,6 hexanetetrol (1,2,5,6-HTO) with the results shown in Table 4.

TABLE 3

| Sample ID | Feed | | | Jacket Temp C. | Pressure PSI | LHSV | H2 flow ml/min |
|---|---|---|---|---|---|---|---|
| | Propylene Glycol % | Sorbitol % | water % | | | | |
| XP1-1116 | 52.8 | 25.4 | 21.7 | 210 | 1800 | 0.4 | 800 |
| XP1-1119 | 52.8 | 25.4 | 21.7 | 210 | 1800 | 0.4 | 800 |
| XP1-1123 | 50 | 25 | 25 | 210 | 1800 | 0.4 | 800 |
| XP1-1124 | 50 | 25 | 25 | 210 | 1800 | 0.5 | 800 |
| XP1-1125 | 50 | 25 | 25 | 210 | 1800 | 0.5 | 800 |
| XP1-1126 | 50 | 25 | 25 | 210 | 1800 | 0.5 | 800 |
| XP1-1204 | 50 | 25 | 25 | 210 | 1800 | 0.5 | 800 |

TABLE 4

| Sample ID | Sorbitol Conversion % | PG % | Molar Selectivity (%) | | | | | |
|---|---|---|---|---|---|---|---|---|
| | | | EG | 1,2-HDO | 1,2-BDO | 1,2,6-HTO | 1,4,5-HTO | 1,2,5,6-HTO |
| XP1-1116 | 99 | 52.5 | 13.23 | 3.14 | 15.76 | 5 | 32.71 | 35.08 |
| XP1-1119 | 99 | 52.39 | 12.43 | 3.33 | 15.58 | 5.36 | 32.15 | 37.83 |
| XP1-1123 | 99 | 48.93 | 11.48 | 3.1 | 13.85 | 5.24 | 28.1 | 37.87 |
| XP1-1124 | 99 | 50.2 | 12.2 | 3.28 | 14.84 | 5.3 | 25.72 | 35.56 |
| XP1-1125 | 99 | 50.32 | 14.03 | 3.83 | 17.12 | 6.22 | 30.11 | 42.01 |
| XP1-1126 | 99 | 49.12 | 11.53 | 3.25 | 13.98 | 5.41 | 27.03 | 38.38 |
| XP1-1127 | 99 | 49.04 | 11.58 | 3.23 | 13.94 | 5.61 | 26.83 | 38.49 |
| XP1-1204 | 99 | 48.83 | 10.46 | 2.99 | 10.26 | 5.51 | 26.54 | 46.12 |

Example 11: Conversion of 1,2,5,6 Hexanetetrol to 2,5-bis(hydroxymethyl)tetrahydrofuran with Sulfuric Acid A solution of 0.6 grams of concentrated sulfuric acid and 36 grams of 1,2,5,6-hexanetetrol was reacted under vacuum (~20 torr) at 120° C. for 1 hour. The solution was cooled to room temperature and then neutralized by adding 50 milliliters of water and 2 grams of calcium carbonate. The solution was filtered and then concentrated under vacuum to obtain about a 96% yield of 2,5-bis(hydroxymethyl)tetrahydrofuran.

Example 12: Conversion of 1,2,5,6 Hexanetetrol to 2,5 bis(hydroxymethyl)tetrahydrofuran with Bismuth Triflate A solution of 110 milligrams of bismuth triflate and 151.41 grams of a sorbitol hydrogenolysis mixture containing 33% wt/wt 1,2,5,6-hexanetetrol was reacted under vacuum (less than 5 torr) at 130° C. for 2 hours The solution was cooled to room temperature. A sample analyzed by high performance liquid chromatography (HPLC) showed full conversion of the 1,2,5,6-hexanetetrol and indicated that 93.4% of the theoretical yield of 2,5-bis(hydroxymethyl) tetrahydrofuran was obtained.

Example 13: Conversion of 1,2,5,6 Hexanetetrol to 2,5 bis(hydroxymethyl)tetrahydrofuran with Scandium Triflate A solution of 89 milligrams of scandium triflate and 163.57 grams of a sorbitol hydrogenolysis mixture containing 33% wt/wt 1,2,5,6-hexanetetrol was reacted under vacuum (less than 5 torr) at 130° C. for 2 hours. The solution was cooled to room temperature. A sample analyzed by HPLC showed full conversion of the 1,2,5,6-hexanetetrol and indicated that 91.3% of the theoretical yield of 2,5-bis (hydroxymethyl)tetrahydrofuran was obtained.

Example 14: Conversion of 1,2,5,6 Hexanetetrol to 2,5-bis(hydroxymethyl)tetrahydrofuran with Bismuth Trilfate A mixture of 544 milligrams of 1,2,5,6 hexanetetrol and 24 milligrams of bismuth triflate was reacted under vacuum (200 torr) at 130° C. for 2 hours. The resulting residue was cooled to room temperature. A sample analyzed by gas chromatography indicated that the residue contained 1.24% (by weight) of the starting hexane-1,2,5,6-tetrol and 61.34% (by weight) of the desired (tetrahydrofuran-2,5,-diyl)dimethanol.

Example 14: Conversion of 1,2,5,6 Hexanetetrol to 2,5-bis(hydroxymethyl)tetrahydrofuran with Phsosphonic Acid A three neck, 500 mL round bottomed flask equipped with a PTFE coated magnetic stir bar was charged with 300 g of a mesophasic, off-white oil comprised of ~42 wt. % 1,2,5,6-hexanetetrol and 3.44 g of phosphonic acid ($H_3PO_3$, 5 mol % relative to HTO). One neck was capped with a ground glass joint, the center with a sleeved thermowell adapter fitted with a thermocouple, and the last a short path condenser affixed to a dry-ice cooled 250 mL pear-shaped receiver. While vigorously stirring, the mixture was heated to 150° C. under vacuum (20 torr) for 4 hours. After this time, the vacuum was broken and residual, light colored oil cooled, and weighed, furnishing 3.06 g. GC analysis indicated that 95 mol % of the HTO had been converted and the selectivity yield for 2,5-bis(hydroxymethyl)tetrahydrofuran was 88% mol/mol.

Example 16: Preparation of tetrahydrofuran-2-methanol from 1,2,5 pentanetriol

A mixture of 1.05 grams of pentane-1,2,5-triol and 57 milligrams of bismuth triflate was reacted under vacuum (200 torr) at 130° C. for 2 hours. The resulting residue was cooled to room temperature. A sample analyzed by gas chromatography indicated that the residue contained 36.24% (by weight) of the starting pentane-1,2,5-triol and 50.37% (by weight) of the desired (tetrahydrofuran-2-yl)methanol.

Example 17: Preparation of 3-Tetrahydrofuranol from 1,2,4 Butanetriol

A mixture of 1.00 grams of 1,2,4 butanetriol and 62 milligrams of bismuth triflate was reacted under vacuum (200 torr) at 130° C. for 2 hours. The resulting residue was cooled to room temperature. A sample analyzed by gas chromatography indicated that the residue contained 12.56% (by weight) of the starting butane-1,2,4-triol and 76.35% (by weight) of the desired tetrahydrofuran-3-ol.

Example 18: Preparation of 5-methyltetrahydrofuran-2-methanol from 1,2,5 Hexanetriol A mixture of 817 milligrams 1,2,5 hexanetriol and 40 milligrams of bismuth triflate was reacted under vacuum (200 torr) at 130° C. for 2 hours. The resulting residue was cooled to room temperature. A sample analyzed by gas chromatography indicated that the starting hexane-1,2,5-triol was completely converted and that the residue contained 75.47% (by weight) of the desired methyltetrahydrofuran-2-methanol. Also produced at a 7.42% weight yield was the isomer 2-methyl-4-tetrahydropyranol.

Example 19 General Analytical Protocol for Ring Cyclization

Upon completion of the reactant dehydrative cyclizations as described in examples 11-18, a sample of the reaction mixture was withdrawn and diluted with enough water to produce a 1-5 mg/mL solution. An aliquot of this was then subjected to high performance liquid chromatography (HPLC) for quantification using an Agilent 1200® series instrument and employing the following protocol: A 10 μL sample was injected onto a 300 mm×7.8 mm BioRad® organic acid column that was pre-equilibrated with an 5 mM sulfuric acid mobile phase and flowed at a rate of 0.800 mL/min. The mobile phase was held isocratic and molecular targets eluting from the column at signature times determined by refractive index detection (RID). A quantitative method for each analyte was established prior to injection, applying linear regression analysis with correlation coefficients of at least 0.995.

What is claimed is:

1. A method of making 2,5-bis(hydroxymethyl)tetrahydrofuran, comprising: contacting a mixture comprising 1,2,5,6-hexanetetrol with an acid catalyst selected from the group consisting of carbonic acid and a water tolerant non-Bronsted Lewis acid in the form of a triflate compound for a time and at a temperature and a pressure sufficient to convert the 1,2,5,6-hexanetetrol to 2,5 bis(hydroxymethyl)tetrahydrofuran.

2. The method of claim 1, wherein the non-Bronsted Lewis acid is selected from the group consisting of bismuth triflate and scandium triflate.

3. The method of claim 1, wherein the reaction mixture is heated to a temperature between 110° C. and 150° C.

4. The method of claim 1, wherein the mixture is contacted with the catalyst under vacuum pressure of between 0.021 MPa and 0.041 MPa (3 and 6 psi).

5. The method of claim 1, wherein the mixture is contacted with the catalyst under vacuum pressure of less than 0.0023 MPa (0.4 psi).

6. The method of claim 1, wherein the acid catalyst is present in an amount between 0.5 mol % and 5 mol % based on the amount of the 1,2,5,6-hexanetetrol.

7. The method of claim 1, further comprising separating the 2,5-bis(hydroxymethyl) tetrahydrofuran from the mixture and contacting the separated 2,5-bis(hydroxymethyl) tetrahydrofuran with a rhenium oxide catalyst further comprising silicon oxide for a time and a temperature sufficient to convert the 2,5-bis(hydroxymethyl)tetrahydrofuran to 1,6 hexanediol.

* * * * *